United States Patent

Ishrak et al.

[11] Patent Number: 6,048,312
[45] Date of Patent: Apr. 11, 2000

[54] METHOD AND APPARATUS FOR THREE-DIMENSIONAL ULTRASOUND IMAGING OF BIOPSY NEEDLE

[76] Inventors: Syed Omar Ishrak, 8035 N. Beach Dr., Fox Point, Wis. 53217; Mir Said Seyed-Bolorforosh, 1824 Oak Creek Dr., Palo Alto, Calif. 94304; William Thomas Hatfield, 1305 Keyes Ave., Schenectady, N.Y. 12309; Todd Michael Tillman, 1514 S. 54th St., West Milwaukee, Wis. 53214; Brian Peter Geiser, 923 Parkview St., Hartland, Wis. 53029; Gregory R. Bashford, N65 W13544 Cobblestone Crt., Menomonee Falls, Wis. 53051; Michael Joseph Washburn, 12920 W. Graham St., New Berlin, Wis. 53151

[21] Appl. No.: 09/139,373

[22] Filed: Aug. 25, 1998

Related U.S. Application Data

[63] Continuation-in-part of application No. 09/064,953, Apr. 23, 1998.

[51] Int. Cl.[7] .................................................... A61B 8/00
[52] U.S. Cl. ..................... 600/443; 600/444; 600/447; 600/440; 128/916
[58] Field of Search .................................... 600/407, 437, 600/440, 443, 447, 454, 459; 128/916; 73/620, 622, 625, 628, 641; 378/8, 41; 367/110, 113, 138; 601/4; 606/1

[56] References Cited

U.S. PATENT DOCUMENTS

| | | | |
|---|---|---|---|
| 4,694,434 | 9/1987 | Von Ramm et al. | 367/7 |
| 4,937,797 | 6/1990 | Snyder et al. | 367/138 |
| 5,065,740 | 11/1991 | Itoh | 128/24 EL |
| 5,488,952 | 2/1996 | Schoolman | 128/916 |
| 5,806,521 | 9/1998 | Morimoto et al. | 600/447 |
| 5,884,627 | 3/1999 | Wakabayashi et al. | 600/447 |
| 5,899,863 | 5/1999 | Hatfield et al. | 600/443 |
| 5,911,691 | 6/1999 | Mochizuki et al. | 600/443 |
| 5,924,986 | 7/1999 | Chandler et al. | 600/443 |

*Primary Examiner*—Marvin M. Lateef
*Assistant Examiner*—Ali M. Imam
*Attorney, Agent, or Firm*—Dennis M. Flaherty; Christian C. Cabou; Phyllis Y. Price

[57] ABSTRACT

A method and an apparatus for three-dimensional ultrasound imaging of a needle-like instrument, such as a biopsy needle, inserted in a human body. The instrument is visualized by transmitting ultrasound beams toward the instrument and then detecting the echo signals using a linear array of transducer elements. The problem of ultrasound being reflected from a biopsy needle in a direction away from the transducer array is solved by steering the transmitted ultrasound beams to increase the angle at which the beams impinge upon the biopsy needle. Ideally the ultrasound beams are perpendicular to the biopsy needle. This increases the system's sensitivity to the needle because the reflections from the needle are directed closer to the transducer array. This can be accomplished using either the B mode or the color flow mode of an ultrasound imaging system. The acquired data for multiple two-dimensional image frames is gathered in memory to form a data volume, which is then processed to form a three-dimensional image (by projection) or a two-dimensional slice taken at an angle through the data volume. In particular, a two-dimensional slice which is coplanar with the inserted biopsy needle can be imaged.

36 Claims, 10 Drawing Sheets

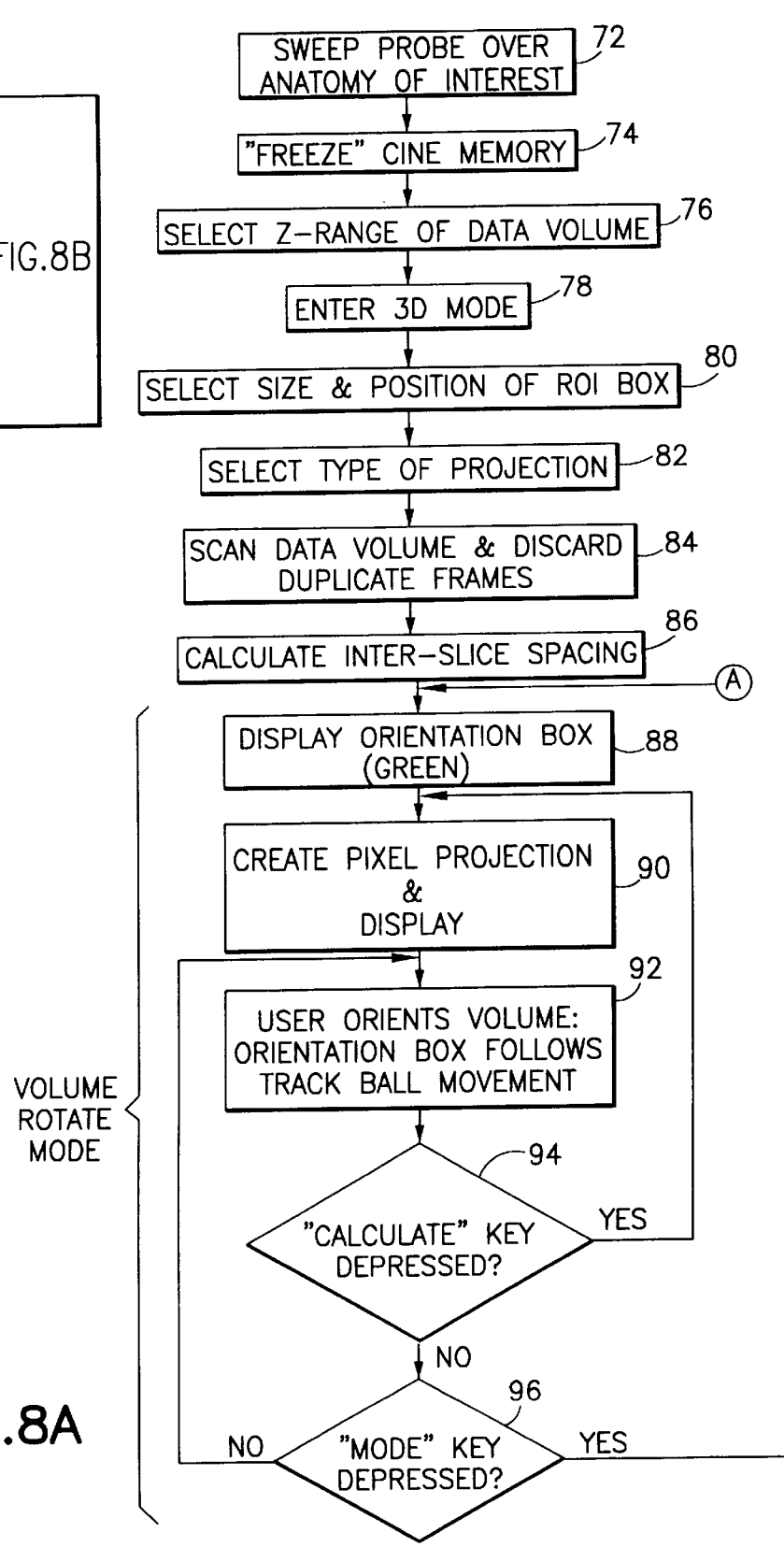

6,048,312

METHOD AND APPARATUS FOR THREE-DIMENSIONAL ULTRASOUND IMAGING OF BIOPSY NEEDLE

RELATED PATENT APPLICATION

This application is a continuation-in-part application of U.S. patent appln. Ser. No. 09/064,953 filed on Apr. 23, 1998.

FIELD OF THE INVENTION

This invention generally relates to ultrasound imaging of the human body. In particular, the invention relates to methods for visualizing an instrument being inserted in the human body during medical diagnosis, surgery or treatment.

BACKGROUND OF THE INVENTION

Conventional ultrasound scanners create two-dimensional B-mode images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In power Doppler imaging, the power contained in the returned Doppler signal is displayed.

Ultrasound imaging is also useful in positioning an instrument at a desired location inside a human body. For example, in order to perform a biopsy on a tissue sample, a biopsy needle must be accurately positioned so that the tip of the biopsy needle penetrates the tissue to be sampled. By tracking the biopsy needle using an ultrasound imaging system, the biopsy needle can be directed toward the target tissue and inserted to the required depth. Thus, by visualizing both the tissue to be sampled and the penetrating instrument, accurate placement of the instrument relative to the tissue can be achieved.

However, in order to visualize the biopsy needle most effectively, it is important to ensure that the incident ultrasound beam is perpendicular with respect to the biopsy needle. The smaller the angle at which the biopsy needle is inserted relative to the axis of the transducer array, i.e., the imaginary line normal to the face of the transducer array, the more difficult it becomes to visualize the needle. A needle is a specular reflector, meaning that it behaves like a mirror with regard to the ultrasound waves reflected off of it. The ultrasound is reflected away from the needle at an angle equal to the angle between the transmitted ultrasound beam and the needle. In a typical biopsy procedure using a linear probe, the geometry is such that most of the transmitted ultrasound energy is reflected away from the transducer array face and thus is poorly detected by the ultrasound imaging system.

Commonly, biopsy needles are inserted into anatomy to obtain a tissue sample. The tissue sample may be in the form of a cyst or tumor mass that needs to be investigated. However, due to the thin and flexible nature of the biopsy needle, sometimes the needle deflects off of the cyst or tumor. This deflection brings into question the validity of the tissue sample.

Thus there is a need for a technique for improving visualization of a needle-like instrument being inserted into a human body so that the position of the needle tip with respect to the surrounding anatomy is clearly shown.

SUMMARY OF THE INVENTION

The present invention is a method and an apparatus for three-dimensional ultrasound imaging of a needle-like instrument, such as a biopsy needle, being inserted in a human body. The instrument is visualized in three dimensions by transmitting ultrasound beams toward the instrument and then detecting the echo signals in each one of a multiplicity of scan planes using a linear array of transducer elements. The acquired data forms a data volume which is processed in accordance with a selected imaging mode. A user interface is designed to allow the operator of an ultrasound imaging system to switch between two-dimensional slices and three-dimensional projections in such a way that it is easy for the operator to visualize the relationship of the two-dimensional slice to the three-dimensional anatomy.

In accordance with the invention, the problem of ultrasound being reflected from a biopsy needle in a direction away from the transducer array is solved by steering the transmitted ultrasound beams to increase the angle at which the beams impinge upon the biopsy needle. Ideally the ultrasound beams are perpendicular to the biopsy needle. This increases the system's sensitivity to the needle because the reflections from the needle are directed closer to the transducer array. This can be accomplished using either the B mode or the color flow mode of the ultrasound imaging system.

In two-dimensional imaging of a biopsy needle, a composite image can be formed comprising a B-mode image frame acquired using a linear transducer array operated to scan without steering (i.e., with beams directed normal to the array) and one or more image frames acquired by causing the linear transducer array to scan with beams steered toward the needle. The latter image frames can be acquired using either the B mode or the color flow mode. If second and third image frames are formed in the B mode, then all three B-mode image frames can be combined in a linear or nonlinear manner to form the composite image. If a second image frame is formed in the color flow mode, then that color image frame is superimposed on the B-mode (gray scale) image frame acquired during the first scan, thereby forming a composite image for display on the display monitor. Alternatively, if second and third image frames are formed in the color flow mode, then the color image frames are combined in a linear or nonlinear manner to form a combined color image, which is then superimposed on the B-mode (gray scale) image frame acquired during the first scan.

In accordance with the present invention, the color and B-mode data for the two-dimensional images are gathered in memory to form a data volume, which is then processed to form a three-dimensional image (by projection) or a two-dimensional slice taken at an angle through the data volume. In particular, a two-dimensional slice which is coplanar with the inserted biopsy needle can be imaged.

DETAILED DESCRIPTION OF THE PREFERRED EMBODIMENTS

Figure 1:
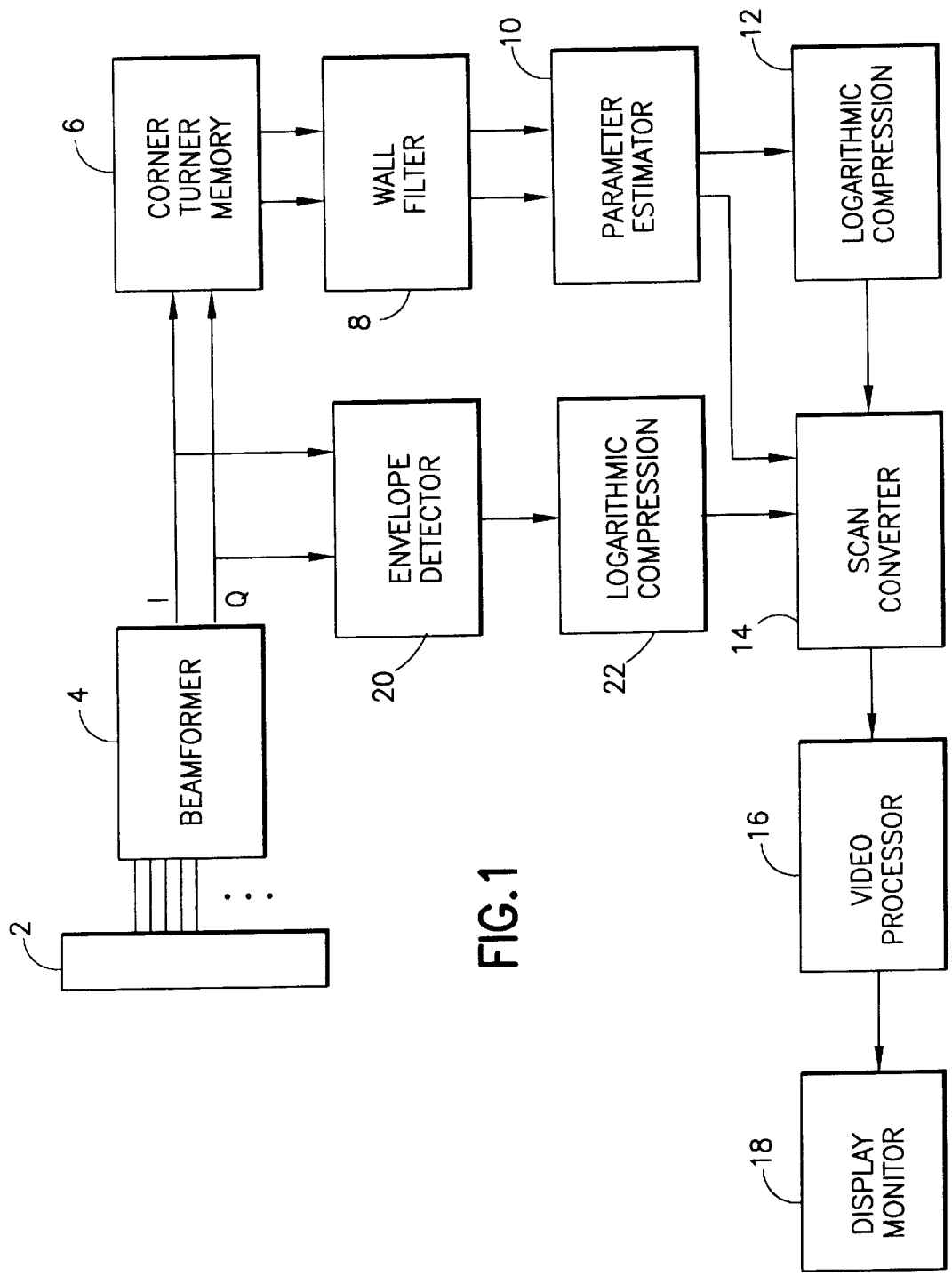
FIG. 1 is a block diagram showing the B mode and color flow mode signal processing chains for an ultrasound imaging system incorporating the present invention.

An ultrasound imaging system incorporating the present invention is shown in FIG. 1. In this system, a linear ultrasound transducer array 2 is activated to transmit a series of multi-cycle (typically 4 to 8 cycles) tone bursts which are focused at the same transmit focal position with the same transmit characteristics. These tone bursts are fired at a pulse repetition frequency (PRF). A series of transmit firings focused at the same transmit focal position are referred to as a "packet". Each transmit beam propagates through the object being scanned and is reflected by ultrasound scatterers in the object.

After each transmit firing, the echo signals detected by the transducer array elements are fed to respective receive channels of a beamformer 4. The receive beamformer tracks echoes under the direction of a master controller (not shown in FIG. 1). The receive beamformer imparts the proper receive focus time delays to the received echo signal and sums them to provide an echo signal which accurately indicates the total ultrasonic energy reflected from a succession of ranges corresponding to a particular transmit focal position. The beamformer also transforms the RF signal into its I/Q components by means of Hilbert bandpass filtering. The I/Q components are then summed in a receive summer (not shown in FIG. 1) for each transmit firing. Hilbert bandpass filtering can alternatively be performed after beam summation. The output of the beamformer 4 may optionally be shifted in frequency by a demodulator (not shown). One way of achieving this is to multiply the input signal by a complex sinusoidal $e^{i2\pi f_d 1}$, where $f_d$ is the frequency shift required.

The I/Q components are then sent to either a B-mode processor or a color flow processor. The B-mode processor incorporates an envelope detector 20 for forming the envelope of the beamsummed receive signal by computing the quantity $(I^2+Q^2)^{1/2}$. The envelope of the signal undergoes some additional B-mode processing, such as logarithmic compression (block 22 in FIG. 1), to form display data which is output to the scan converter 14.

In general, the display data is converted by the scan converter 14 into X-Y format for video display. The scan-converted frames are passed to a video processor 16, which maps the video data to a gray-scale mapping for video display. The gray-scale image frames are then sent to the video monitor 18 for display.

The images displayed by the video monitor 18 are produced from an image frame of data in which each datum indicates the intensity or brightness of a respective pixel in the display. An image frame may, e.g., comprise a 256×256 data array in which each intensity datum is an 8-bit binary number that indicates pixel brightness. The brightness of each pixel on the display monitor 18 is continuously refreshed by reading the value of its corresponding element in the data array in a well-known manner. Each pixel has an intensity value which is a function of the backscatter cross section of a respective sample volume in response to interrogating ultrasonic pulses and the gray map employed.

A conventional ultrasound imaging system typically employs a variety of gray maps, which are simple transfer functions of the raw image data to display gray levels. Multiple gray maps are supported so that different maps may be used depending on the raw image data.

In the color flow mode, the I/Q components are stored in a corner turner memory 6, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 8. In accordance with the preferred embodiment of the invention, each wall filter acts as either an all-pass filter or a high-pass filter with extremely low cutoff frequency. In the former instance, the wall filter has a single coefficient which is unity, i.e., [1]. In the latter instance, the filter coefficients, for example, may be [−0.3, −0.2, 1.0, −0.2, −0.3], with a pulse repetition frequency of 200 Hz.

Given the angle θ between the insonifying beam and the flow axis, the magnitude of the velocity vector can be determined by the standard Doppler equation:

$$v = cf_d/(2f_0\cos\theta) \qquad (1)$$

where c is the speed of sound in blood, $f_0$ is the transmit frequency and $f_d$ is the motion-induced Doppler frequency shift in the backscattered ultrasound.

The wall-filtered outputs are fed into a parameter estimator 10, which converts the range cell information into the intermediate autocorrelation parameters N, D, and R(0). N and D are the numerator and denominator for the autocorrelation equation, as shown below:

$$N = \sum_{i=1}^{M-1} (I_i Q_{i+1} - I_{i+1} Q_i) \qquad (2)$$

$$D = \sum_{i=1}^{M-1} (I_i I_{i+1} + Q_i Q_{i+1}) \qquad (3)$$

where $I_i$ and $Q_i$ are the input data for firing i, and M is the number of firings in the packet. R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \quad (4)$$

R (0) indicates the power in the returned ultrasound echoes.

A processor in parameter estimator 10 converts N and D into a magnitude and phase for each range cell. The equations used are as follows:

$$|R(T)| = \sqrt{N^2 + D^2} \quad (5)$$

$$\phi(R(T)) = \tan^{-1}\left[\frac{N}{D}\right] \quad (6)$$

The parameter estimator 10 processes the magnitude and phase values into estimates of power, velocity and turbulence. The phase is used to calculate the mean Doppler frequency, which is proportional to the velocity as shown below; R(0) and |R(T)| (magnitude) are used to estimate the turbulence.

The mean Doppler frequency is obtained from the phase of N and D and the pulse repetition time T:

$$\bar{f} = \frac{1}{2\pi T}\tan^{-1}\left[\frac{N}{D}\right] = \frac{1}{2\pi T}(\phi(R(T))) \quad (7)$$

The mean velocity is calculated using the Doppler shift equation:

$$\bar{v} = \frac{\bar{f}}{f_0}\frac{c}{2\cos\theta} \quad (8)$$

The parameter estimator 10 does not calculate the mean Doppler frequency as an intermediate output, but calculates $\bar{v}$ directly from the phase output of a processor using a lookup table. Typically the power estimates are compressed before scan conversion, e.g., using logarithmic compression (block 12 in FIG. 1)

In the color flow mode, the color estimates (i.e., power or velocity) are sent to scan converter 14, which converts the color images into X-Y format for video display. The scan-converted frames are passed to a video processor 16, which maps the video data to a display color map for video display. The color flow image frames are then sent to the video monitor 18 for display.

Figure 2:
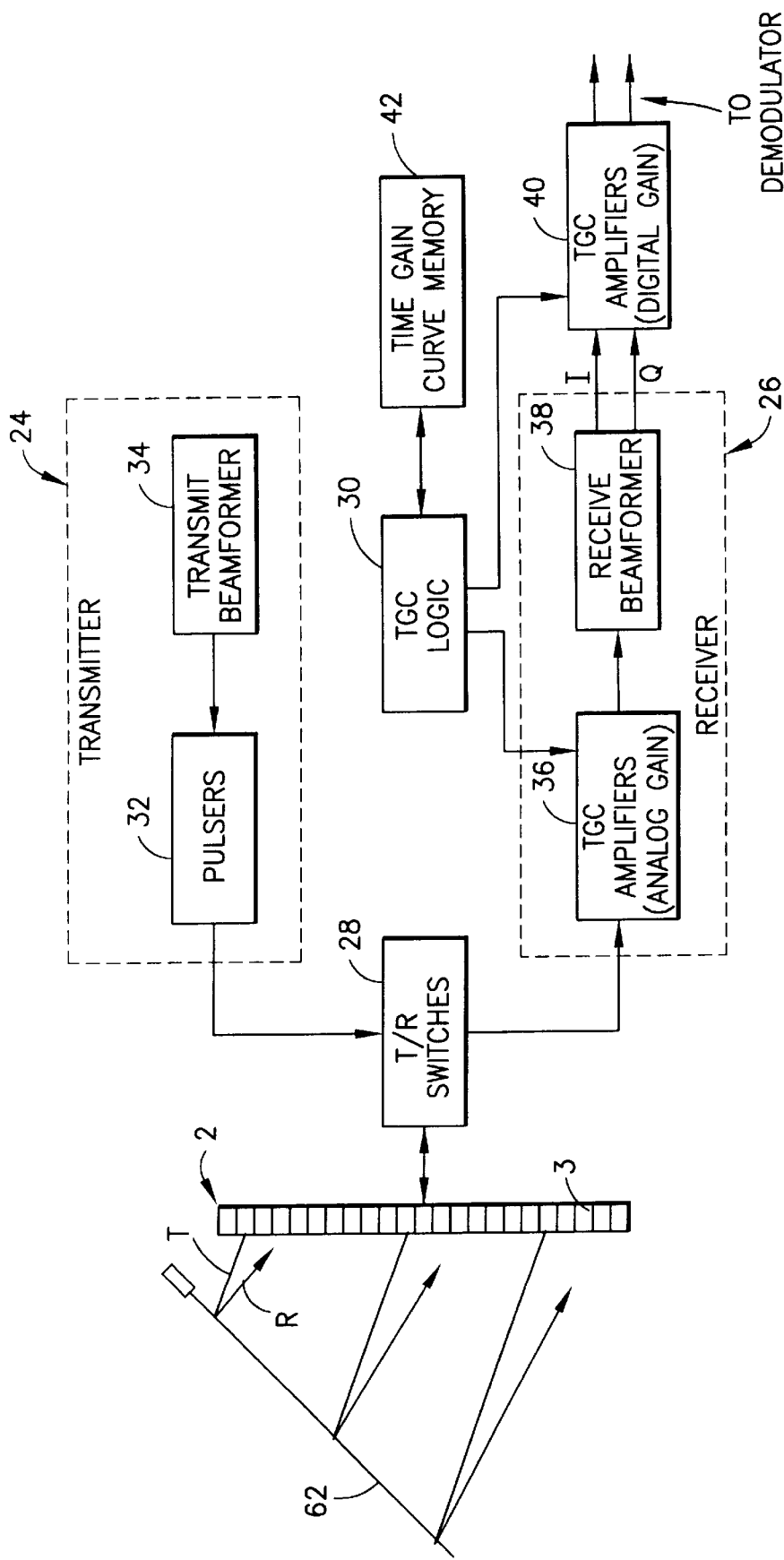
FIG. 2 is a block diagram showing the front end of the ultrasound imaging system shown in FIG. 1, with the biopsy needle shown in positional relationship with the transducer array.

The front end of the ultrasound imaging system is shown in FIG. 2 in more detail. The transducer array 2 comprises a plurality of separately driven transducer elements 3, each of which produces a burst of ultrasonic energy when energized by a pulsed waveform produced by a transmitter 24. The ultrasonic energy reflected back to transducer array 2 from the object under study is converted to an electrical signal by each receiving transducer element 2' and applied separately to a receiver 26 through a set of transmit/receive (T/R) switches 28. The T/R switches 28 are typically diodes which protect the receive electronics from the high voltages generated by the transmit electronics. The transmit signal causes the diodes to shut off or limit the signal to the receiver. Transmitter 24 and receiver 26 are operated under control of a host computer or master controller (not shown in FIG. 2) responsive to commands by a human operator. A complete scan is performed by acquiring a series of echoes in which transmitter 24 is gated ON momentarily to energize each transducer element 3, and the subsequent echo signals produced by each transducer element 3 are applied to receiver 26. A channel may begin reception while another channel is still transmitting. The receiver 26 combines the separate echo signals from each transducer element to produce a single echo signal which is used to produce a line in an image on the display monitor.

Under the direction of a host computer, the transmitter 24 drives transducer array 2 such that the ultrasonic energy is transmitted as a directed focused beam. To accomplish this, respective time delays are imparted to a multiplicity of pulsers 32 by a transmit beamformer 34. The host computer determines the conditions under which the acoustic pulses will be transmitted. With this information, the transmit beamformer 34 will determine the timing and the amplitudes of each of the transmit pulses to be generated by pulsers 32. The pulsers 32 in turn send the transmit pulses to each of the elements 3 of the transducer array 2 via the T/R switches 28, which protect the time-gain control (TGC) amplifiers 36 from the high voltages which may exist at the transducer array. By appropriately adjusting the transmit focus time delays in a conventional manner, an ultrasonic beam can be directed and focused to form a steered transmit beam. A series of steered beams are transmitted as the transmit aperture is shifted across the linear transducer array.

The echo signals produced by each burst of ultrasonic energy reflect from scatterers located at successive ranges along each transmit beam. The echo signals are sensed separately by each transducer element 3 and a sample of the magnitude of the echo signal at a particular point in time represents the amount of reflection occurring at a specific range. Due to the differences in the propagation paths between a reflecting point and each transducer element 3, the echo signals will not be detected simultaneously and their amplitudes will not be equal. Receiver 26 amplifies the separate echo signals via a respective TGC amplifier 36 in each receive channel. The amount of gain provided by the TGC amplifiers 36 is a direct function of the depth from which the receive signals are returned. The amplified echo signals are then fed to the receive beamformer 38.

Under the direction of the host computer, the receive beamformer 38 tracks the direction of the transmitted beam. The receive beamformer 38 imparts the proper time delays to each amplified echo signal and sums them to provide an echo signal which accurately indicates the total ultrasonic energy reflected from a point located at a particular range along one ultrasonic beam. The receive focus time delays are computed in real-time using specialized hardware or are read from a lookup table. The receive channels also have circuitry for filtering the received pulses and forming the I/Q components. The time-delayed I/Q component signals are then summed and output to respective TGC amplifiers 40, which again apply a depth-dependent gain.

Figure 4:
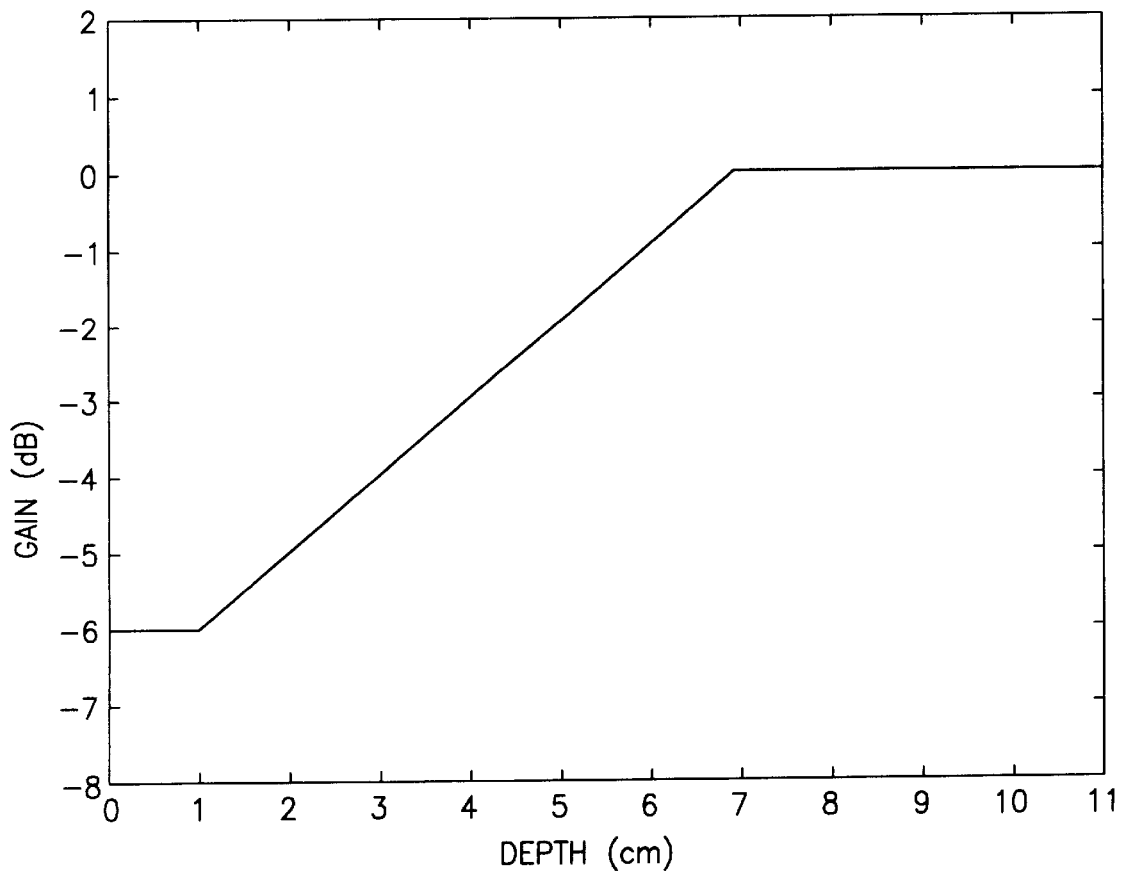
FIG. 4 is a graph showing a depth-dependent gain curve employed in a preferred embodiment of the invention.

An exemplary depth-dependent gain curve for use in the invention is depicted in FIG. 4. This curve can be used if the target location for the biopsy needle is 2 to 6 cm and it is desired to suppress clutter from the 1-cm-deep near field in front of the transducer array. This special gain curve applies a constant small gain to near-field reflections, a constant large gain to far-field reflections and a linearly ramped gain to mid-field reflections, the linear ramp extending from the small gain to the large gain. This depth-dependent gain curve accentuates reflections from the middle field where the needle resides and attenuates reflections from the near field, thereby reducing clutter due to bright reflections from ultrasound scatterers located between the biopsy needle and the transducer array.

The gain curve shown in FIG. 4 is added to the conventional TGC curve (basically a linear ramp increasing with depth). The resulting time-gain curve is stored in memory 42 (see FIG. 2). The gains stored in memory 42 are retrieved as a function of depth by the TGC logic 30. In particular, the time-gain curve is partitioned into analog gain and digital gain. The analog portion of the depth-dependent gain controls the gain of TGC amplifiers 36; the digital portion of the depth-dependent gain controls the gain of TGC amplifiers 40. It should be appreciated, however, that partitioning of the depth-dependent gain is not necessary to carry out the present invention. Partitioning is useful in situations where the hardware (e.g., the analog-to-digital converters in the receive beamformer) cannot tolerate the full depth-dependent gain. In this case, part of the depth-dependent gain is applied after the gain-limited hardware and part is applied before the gain-limited hardware. Where this is not the case, the entire depth-dependent gain can be applied at TGC amplifiers 36.

Figure 3:
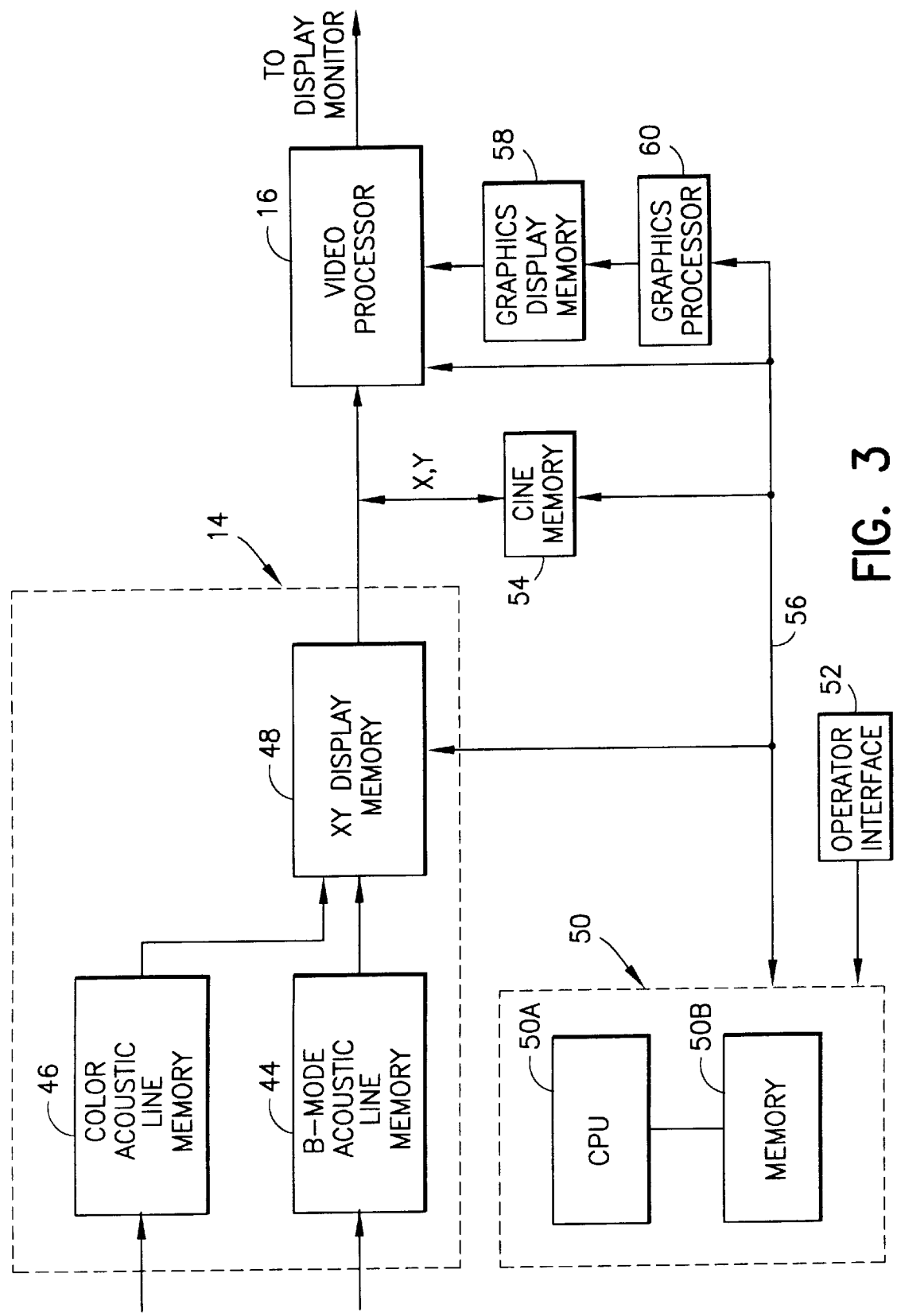
FIG. 3 is a block diagram showing the back end of the ultrasound imaging system shown in FIG. 1.

Referring to FIG. 3, system control is centered in the host computer 50, which accepts operator inputs through an operator interface 52 and in turn controls the various subsystems. The host computer 50 also generates the system timing and control signals. The host computer 50 comprises a central processing unit (CPU) 50A and a random access memory 50B. The CPU 50A is programmed to control the gain applied by the TGC amplifiers, the mapping applied by the video processor and the formation of the composite image from multiple image frames of data.

The scan converter 14 comprises a B-mode acoustic line memory 44 for scan converting B-mode data, a color acoustic line memory 46 for scan converting color flow data and an XY display memory 48 for storing each frame of scan-converted data in a respective one of a bank of frame memories. The data stored in the acoustic line memories is transformed to appropriately scaled Cartesian coordinate pixel display data.

If the image to be displayed is a combination of two or more B-mode frames, then the B-mode data is retrieved from the XY display memory 48 by the CPU 50A and combined to form a single frame of B-mode data. That frame is then returned to the XY display memory 48 and passed to the video processor 16, which maps the B-mode data to a gray map for video display. That frame is also captured in a cine memory 54.

If the image to be displayed is a combination of one B-mode frame and one color flow frame, then both frames are passed to the video processor 16, which maps the B-mode data to a gray map and maps the color flow data to a color map for video display. In the final displayed image, the color pixel data is superimposed on the gray-scale pixel data.

If the image to be displayed is a combination of one B-mode frame and two or more color flow frames, then the color flow data is retrieved from the XY display memory 48 by the CPU 50A and combined to form a single frame of combined color flow data. That frame of combined color flow data is then returned to the XY display memory 48, which passes the B-mode and combined color flow frames to the video processor 16. Again the video processor maps the B-mode data to a gray map and maps the color flow data to a color map for video display. At the same time the B-mode and combined color flow frames are captured in the cine memory 54.

Figure 5:
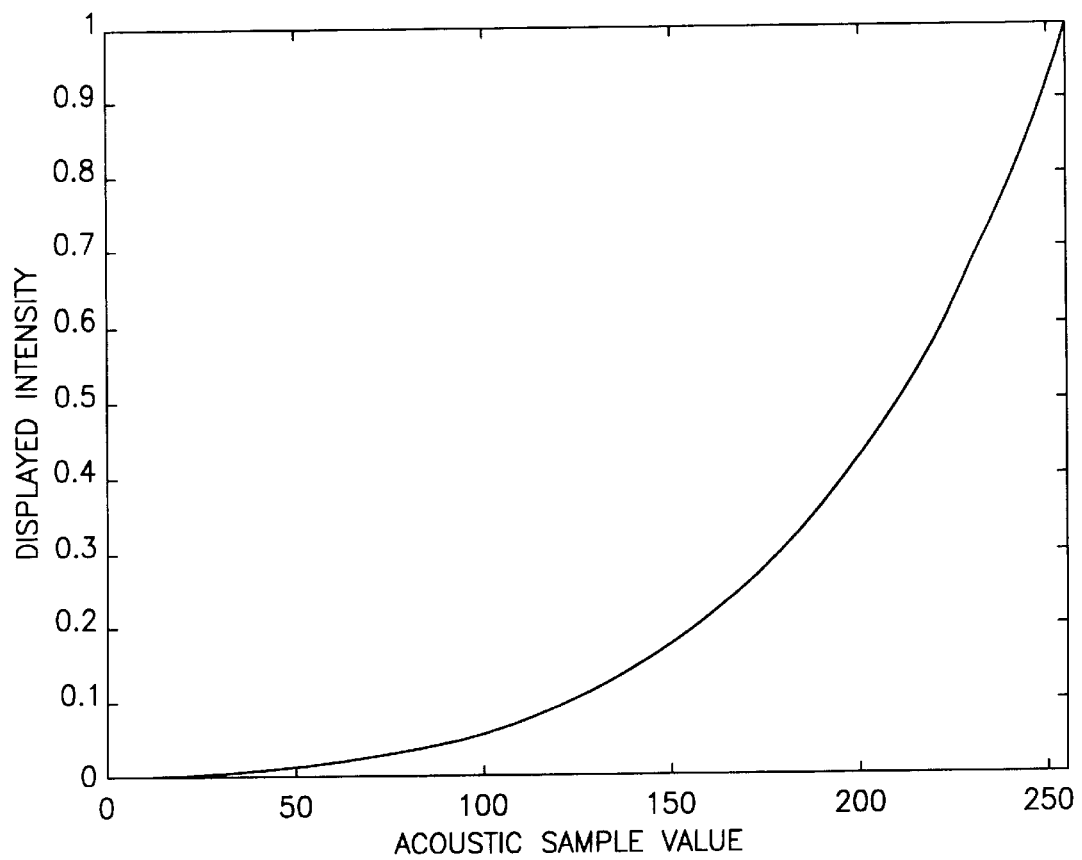
FIG. 5 is a graph showing an acoustic sample value-to-display intensity mapping employed in the preferred embodiment of the invention. The acoustic sample value may represent either intensity, power or velocity.

In accordance with a further feature of the invention, a special color or gray-scale map, stored in the video processor 16, is employed so that large acoustic sample values are displayed with heightened pixel intensity. An exemplary acoustic sample value/display intensity mapping is shown in FIG. 5. The result is that the needle is highlighted in the final composite image. A special gray-scale map need not be used when a color flow image is superimposed on a B-mode background image.

In the normal two-dimensional imaging mode, the composite image of biopsy needle 62 (see FIG. 2) comprises a B-mode image frame acquired by operating linear transducer array 2 to scan without steering (i.e., with beams directed normal to the array) and a second image frame acquired by causing the linear transducer array to scan with beams steered toward the needle at a constant steering angle. Steered beams T and reflected beams R are shown in FIG. 2. The second image frame can be acquired using either the B mode or the color flow mode.

If the second image frame is formed in the B mode, then the two B-mode image frames can be combined in a linear or nonlinear manner by the host computer 50 to form the composite image. For example, the two B-mode image frames of data can be combined in a linear manner by summing or computing the average intensity value from intensity values corresponding to a particular pixel in the two B-mode image frames. Alternatively, the two B-mode image frames can combined in a nonlinear manner, e.g., by selecting the maximum or by inputting the two intensity values into a nonlinear lookup table. The final intensity values are then returned to the XY display memory and output to the video processor 16, which maps the composite image frame for display using a gray scale. Preferably, the gray map is of the type represented in FIG. 5. If the second image frame is formed in the color flow mode, then the video processor maps the B-mode data using a gray map and maps the color flow mode data using a color map. These image frames are then superimposed on the display monitor. Preferably, the color map is of the type represented in FIG. 5. In both instances, the data output from the XY display memory 48 to the video processor 16 is captured by the cine memory 54.

In accordance with another preferred embodiment of the invention, a composite image of a biopsy needle can be made when the exact position of the biopsy needle is undetermined. In this case, the first scan is again a normal B-mode image acquired by operating linear transducer array 2 to scan without steering. A second image frame of data is acquired by causing the linear transducer array to scan with beams steered to the left (at a constant first steering angle) and then a third image frame of data is acquired by causing the linear transducer array to scan with beams steered to the right (at a constant second steering angle). The second and third image frames can be acquired using either the B mode or the color flow mode.

If the second and third image frames are formed in the B mode, then the three B-mode image frames can be combined by the host computer 50 in a linear or non-linear manner to form the composite image. For example, the three B-mode image frames of data can be combined in a linear manner by summing or computing the average intensity value from the intensity values corresponding to a particular pixel in the three B-mode image frames. Alternatively, the three B-mode image frames can be combined in a nonlinear manner, e.g., by selecting the maximum or by inputting the three intensity values into a nonlinear lookup table. The final intensity values of the composite image are returned to the XY display memory 48 and then mapped by video processor 16 for display using the gray map shown in FIG. 5.

If the second and third images are formed in the color flow mode, then the two image frames of power or velocity values can be combined by the host computer 50 in a linear or nonlinear manner, as previously described, to form a combined color flow image. This combined color flow image is returned to the XY display memory 48 and sent to the video processor along with the B-mode image frame acquired during the first scan. As previously described, the video processor then maps the B-mode data using a gray map and maps the combined color flow mode data using a color map. These mapped image frames are then superimposed on the display monitor. Preferably, the color map is again of the type represented in FIG. 5, i.e., the color map accentuates the bright reflections from the specular ultrasound reflector while attenuating the weaker reflections from blood and tissue.

Referring to FIG. 3, system control is centered in host computer 50, which accepts operator inputs through operator interface 52 (e.g., a keyboard and a track-ball) and in turn controls the various subsystems. (In FIG. 3, the system control lines from the host computer to the various subsystems have been omitted for the sake of simplicity.) During scanning of the probe, a long sequence of the most recent images are stored and continuously updated automatically in cine memory 54. Some systems are designed to save the R-θ acoustic images, while other systems store the X-Y video images. The image loop stored in cine memory 54 can be reviewed on the display monitor via track-ball control (interface 52), and a section of the image loop can be selected for hard disk storage. For an ultrasound scanner with free-hand three-dimensional imaging capability, the selected image sequence stored in cine memory 54 is transferred to the host computer 50 for three-dimensional reconstruction. The result is written back into another portion of the cine memory or to scan converter memory, from where it is sent to the display monitor via video processor 16.

A multiplicity of successive frames of B-mode and color flow mode data are stored in cine memory 16 on a first-in, first-out basis. The cine memory is like a circular image buffer that runs in the background, continually capturing image data that is displayed in real time to the user. When the user freezes the system (by depressing the FREEZE key on the interface 22), the user has the capability to view image data previously captured in cine memory.

The imaging system also has the capability to superimpose graphical symbols on any ultrasound image. The superimposition of graphics on the image frame is accomplished in the video processor 16, which receives the ultrasound image frame from the XY display memory 48 and the graphics data from a graphics display memory 58. The graphics data is processed and input into the graphics display memory 58 by a graphics processor 60, which is synchronized with the other subsystems by the host computer 50.

The CPU 50A has memory for storing routines used in transforming an acquired volume of imaging data into a multiplicity of three-dimensional projection images taken at different angles. The CPU 50A controls the XY display memory 48 and the cine memory 54 via the system control bus 56. In particular, the CPU 50A controls the flow of data from the acoustic line memories 44 and 46 or from the XY display memory 48 of the scan converter 14 to the video processor 16 and to the cine memory 54, and from the cine memory to the video processor 16 and to the CPU 50A itself. Each frame of imaging data, representing one of a multiplicity of scans or slices through the object being examined, is stored sequentially in the acoustic line memories 44 and 46, in the XY display memory 48 and in the video processor 16. In parallel, image frames from either the acoustic line memories or the XY display memory are stored in cine memory 54. A stack of frames, representing the scanned object volume, is stored in cine memory 54, forming a data volume comprising B-mode intensity data and color velocity or power Doppler data.

Two-dimensional ultrasound images are often hard to interpret due to the inability of the observer to visualize the two-dimensional representation of the anatomy being scanned. However, if the ultrasound probe is swept over an area of interest and two-dimensional images are accumulated to form a three-dimensional data volume, the anatomy becomes much easier to visualize for both the trained and untrained observer.

In order to generate three-dimensional images, the CPU 50A can transform a source data volume retrieved from cine memory 54 into an imaging plane data set. The successive transformations may involve a variety of projection techniques such as maximum, minimum, composite, surface or averaged projections made at angular increments, e.g., at 10° intervals, within a range of angles, e.g., +90° to −90°. Each pixel in the projected image includes the transformed data derived by projection onto a given image plane.

In free-hand three-dimensional ultrasound scans, a transducer array (1D to 1.5D) is translated in the elevation direction to acquire a substantially parallel set of image planes through the anatomy of interest. These images can be stored in the cine memory and later retrieved by the system computer for three-dimensional reconstruction. If the spacings between image frames are known, then the three-dimensional volume can be reconstructed with the correct aspect ratio between the out-of-plane and scan plane dimensions. If, however, the estimates of the interslice spacing are poor, significant geometric distortion of the three-dimensional object can result.

The ultrasound imaging system collects B-mode, color velocity and power Doppler data in the cine memory on a continuous basis. As the probe is swept over an area of the anatomy, using either a free-hand scanning technique or a mechanical probe mover of some sort, a three-dimensional volume is stored in the cine memory. The distance the probe was translated may be determined by a number of techniques. The user can provide an estimate of the distance swept. If the probe is moved at a constant rate by a probe mover, the distance can easily be determined. Alternatively, a position sensor can be attached to the probe to determine the position of each slice. Markers on the anatomy or within the data could also provide the required position information. Yet another way would be to estimate the scan plane displacements directly from the degree of speckle decorrelation between successive image frames. Once the data volume has been acquired, the central processing unit can then provide three-dimensional projections of the data as well as arbitrary slices through the data volume.

Figure 6:
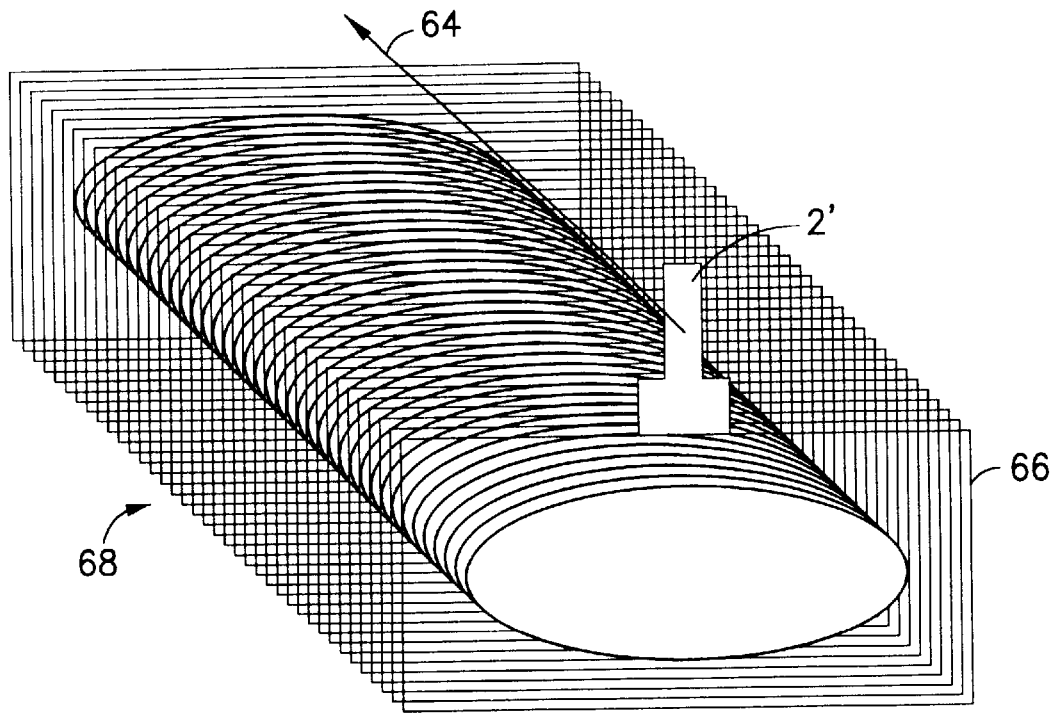
FIG. 6 is a diagram depicting a volume of data acquired by linearly scanning an ultrasound probe in a direction perpendicular to the scan plane of the probe.
Figure 7:
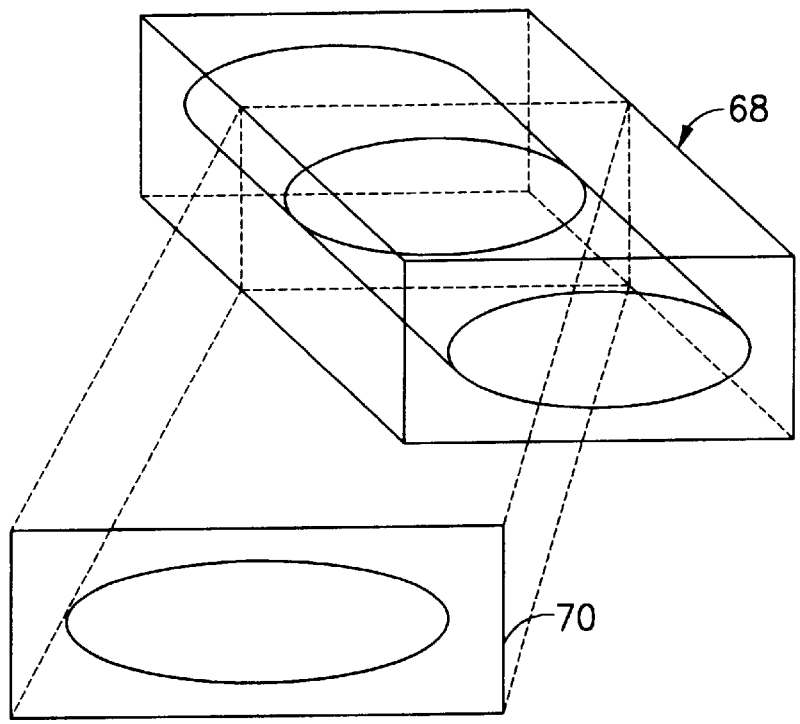
FIG. 7 is a diagram depicting an individual slice at an arbitrary angle obtained by reformatting the data volume depicted in FIG. 6.

Referring to FIG. 6, if the ultrasound probe 2' is swept (arrow 64 indicates a linear sweep) over an area of a body (either by hand or by a probe mover), such that the interslice spacing is known, and the slices 66 are stored in memory, a three-dimensional data volume 68 can be acquired. The data volume can be processed (e.g., using projection onto an imaging plane) to form a three-dimensional view of the area of interest. In addition, the data can be reformatted to produce an individual slice 70 at an arbitrary angle (see FIG. 7), thus allowing the user to get the exact view desired regardless of the anatomy under investigation. For example, slice 70 can be selected so that the biopsy needle is coplanar with the slice plane. Algorithms for producing three-dimensional projections of two-dimensional data are well known, as are techniques for reformatting data to produce arbitrary slices through a data set. For example, to accomplish three-dimensional ultrasound imaging, the pixel projections can be constructed in CPU 50A, which performs a series of transformations using the ray-casting algorithm disclosed in U.S. Pat. No. 5,226,113 to Cline, the contents of which are specifically incorporated by reference herein.

In accordance with a preferred embodiment of the invention, in a "volume rotate" mode, the display screen displays an orientation box along with a three-dimensional projected image generated from a defined data volume. The orientation box provides a visual indication of the shape and orientation of that defined data volume. In the "volume rotate" mode, a biopsy needle can be imaged in relation to a three-dimensional image of the anatomical structure in which the biopsy needle is inserted.

In a "cut plane" mode, a movable polygon representing a selected two-dimensional slice is displayed inside a stationary orientation box. The polygon provides a visual indication of the orientation and position of the slice relative to the defined data volume. The operator may use a track-ball to scroll through the data volume in order to display a desired two-dimensional slice. The polygon is moved inside the orientation box as a function of the track-ball movement to indicate the position of a two-dimensional slice relative to the defined data volume. When the track-ball is stopped, the position of the polygon relative to the orientation box is frozen and the reformatted slice having a corresponding position relative to the defined data volume is displayed. In a "cut plane rotate" mode, a stationary polygon representing a selected two-dimensional slice is displayed inside a rotatable orientation box. The operator moves a track-ball to rotate the orientation box. The shape of the polygon changes to conform to the changing shape of the two-dimensional slice. When the track-ball is stopped, the orientation of the orientation box relative to the polygon is frozen and the reformatted slice having a position corresponding to the position of the polygon is displayed. Using the "cut plane" mode, the image plane can be positioned to intersect the biopsy needle in the middle of the image. Then the "cut plane rotate" mode can be used to rotate the image plane until the biopsy needle is coplanar with the image plane.

Figure 8B:
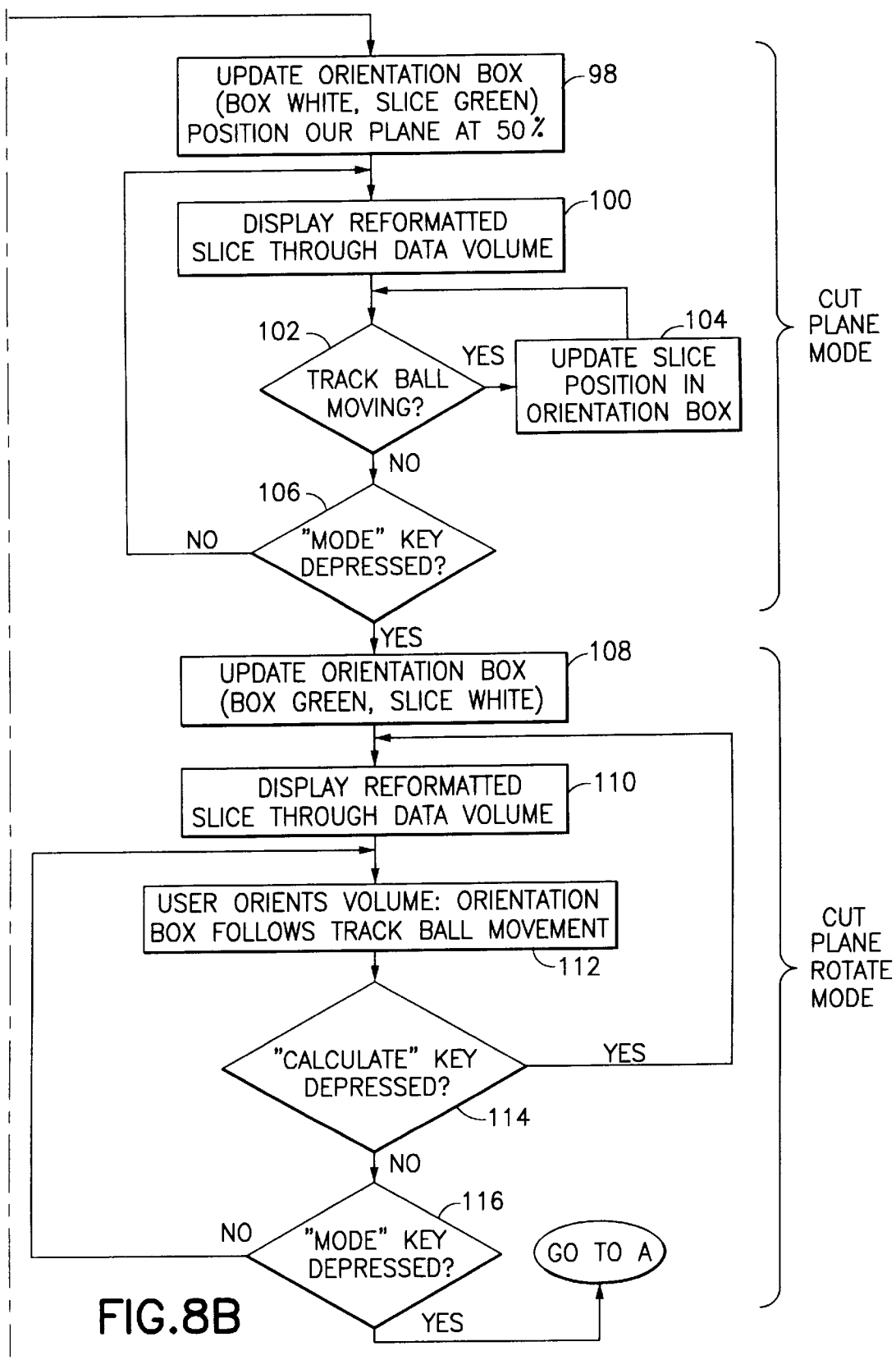
FIG. 8 (presented on two sheets as FIGS. 8A and 8B) is a flow chart showing an acquisition and display procedure employed in the preferred embodiment of the invention.
Figure 9:
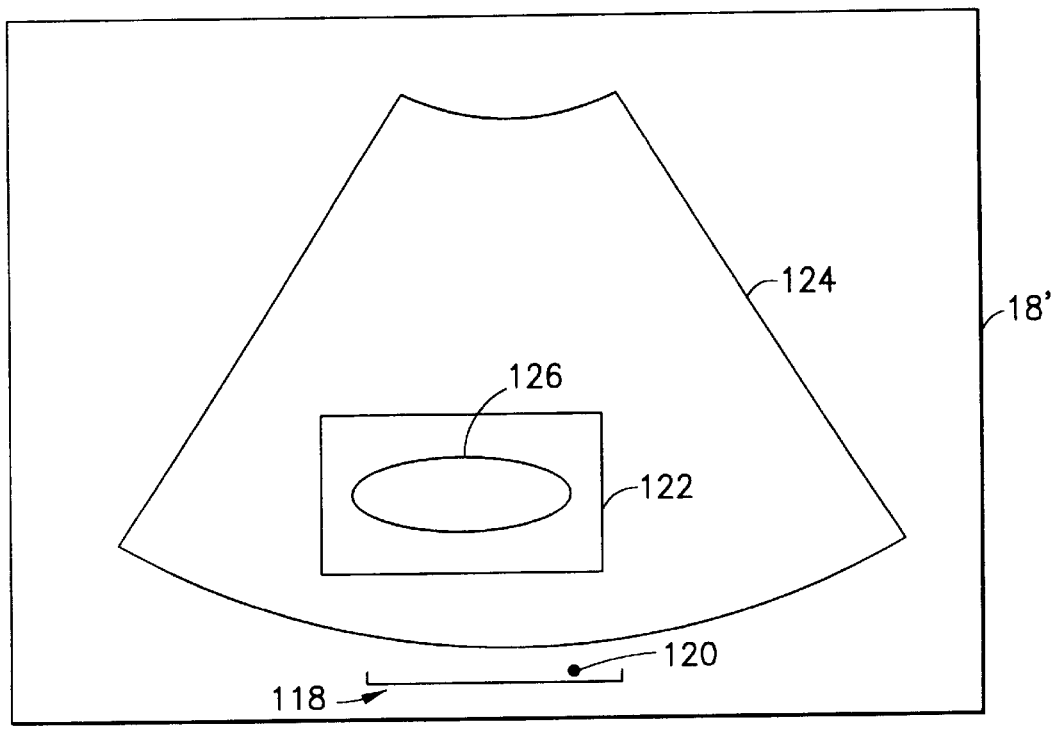
FIG. 9 is a diagram depicting a display of a sector scan ultrasound image with graphics indicating a user-defined volume of interest.

FIGS. 8A and 8B shows a flow chart of the acquisition and display procedure. Referring to FIG. 8A, the user begins by sweeping the ultrasound probe over an area of interest (step 72). For example, the sweep may be acquired by a free-hand sweep in a linear or rocking motion. Once the data is acquired, the user "freezes" the cine memory (step 74) by depressing the FREEZE key and then selects the range of cine memory frames (slices) to be included in the Z-dimension of the data volume (step 76). The operator accomplishes the latter step by moving a track-ball. As seen in FIG. 9, a Z-dimension select gauge 118 appears on the display screen 18' when the track-ball is moved. The track-ball is then used to control the position of an indicator 120 relative to the gauge 118. The indicator can be moved to a desired left end point and then the left end point is locked by depression of predetermined key on the operator interface. Then the indicator can be moved to a desired right end point and then the right end point is locked by depression of the same predetermined key. This establishes the slices to be included in the data volume. The operator then enters the particular "3D mode" desired, i.e., the "reslice" mode, by depressing the appropriate key on the interface (step 78).

Upon entering the re-slice mode, the operator must first select the XY-dimension and location of the data volume (step 80). This step is accomplished by manipulating a region of interest box 122 (shown in FIG. 9) which appears in a default position on the display screen 18' in response to depression of the re-slice mode key. The region of interest box 122 can be sized and translated in X and Y to encompass an imaged structure 126 which appears on the sector scan image 124. The region of interest box 122 is translated by moving the track-ball and is sized by operation of a four-sided rocker switch incorporated in the operator interface. For example, the rocker switch is programmed so that the region of interest increases in size in the Y dimension when the switch is moved downward; decreases in size in the Y dimension when the switch is moved upward; increases in size in the X dimension when the switch is moved rightward; and decreases in size in the X dimension when the switch is moved leftward.

After the data volume has been defined, the operator selects (step 82 in FIG. 8A) the type of three-dimensional projection desired (minimum or maximum pixel projection, surface, composite, etc.) and presses a render key. In accordance with the preferred embodiment, a composite image of projected B-mode data and projected color flow mode data is formed using maximum pixel projection on both B-mode and color flow mode data. Alternatively, minimum pixel projection can be applied to the B-mode data while maximum pixel projection is used on the color flow data. The defined data volume is then retrieved from cine memory 54 (see FIG. 3) by the host computer 50. The host computer scans the retrieved data for duplicate frames and discards them (step 84). The host computer then calculates the interslice spacing for the data set (step 86). (The interslice spacing is assumed to be constant over the length of the data volume.) For example, the inter-slice spacing can be calculated using the adaptive speckle correlation technique disclosed in U.S. patent application Ser. No. 09/045,780 filed on Mar. 20, 1998, the disclosure of which is incorporated by reference herein.

After the inter-slice spacing has been calculated, the system enters a "volume rotate" mode, which is one of three sub-modes included in the so-called "re-slice" mode. Referring to FIG. 3, in the "volume rotate" mode, signals representing a colored (e.g., green) orientation box are generated by the graphics processor 60, arranged in XY format in the graphics display memory 58 and then sent to the video processor 16. The video processor causes a green orientation box to be displayed on the display screen (step 88 in FIG. 8A). At the same time the host computer performs the selected projection of the defined data volume based on the calculated interslice spacing (step 90). The projected three-dimensional image is sent to the XY display memory 48 and then on to the video processor 16. The projected three-dimensional image is also captured by the cine memory 54. The video processor 16 causes the projected three-dimensional image to be displayed on display screen along with the orientation box. Both the orientation box and the initial projection are oriented with the Z axis pointing into the screen, the Y axis vertical, and the X axis horizontal, i.e., the orientation box appears as a rectangle having X and Y dimensions proportional to the X and Y dimensions of the selected region of interest. The data slices are acquired along the Z axis. This is defined to be the zero angle projection.

Figure 10:
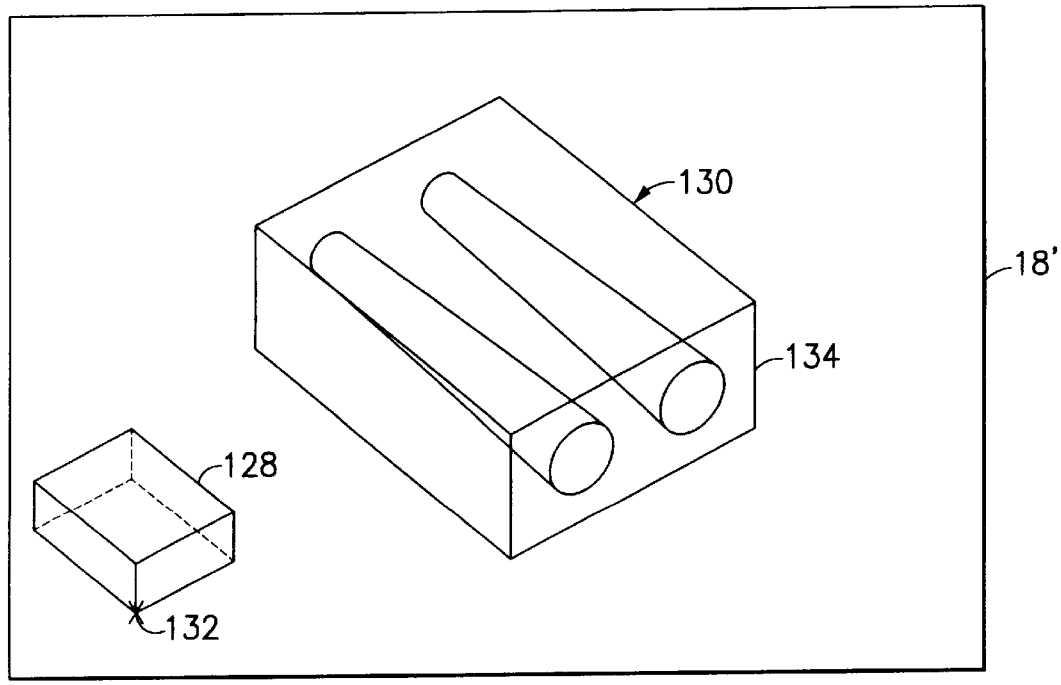
FIG. 10 is a diagram depicting a display of a projected ultrasound image made at an arbitrary angle with graphics indicating the orientation of the data volume.

In the "volume rotate" mode, the operator can use the track-ball to rotate the orientation box about the X and Y axes. Rotation about the Z axis is performed using a separate rotary knob on the operator interface. The orientation box follows the movement of the track-ball and rotary knob in "real-time" so that the user can orient the box as desired (step 92). The rotational position of each axis is shown on the display panel. When the position is set, the user depresses the "calculate" key (step 94), which causes the system to display a new projection of the three-dimensional data set (step 90) at the orientation indicated by the orientation box. FIG. 10 shows an exemplary projection 130 at an arbitrary angle indicated by the orientation box 128. The orientation box has a marker 132 in the lower front left corner while the back corners of the box are dashed to aid the user in distinguishing the front and back of the box. As an aid to visualization, a box 134 is overlaid on the projection 130 which matches the orientation box 128 and is depth shaded to appear to become darker as the box goes towards the "back" of the data volume. The user may reposition the orientation box 128 with the track-ball and rotary knobs and re-project as many times as desired. In addition, rotations of plus or minus 900 may be made with special keys on the operator interface.

Figure 11:
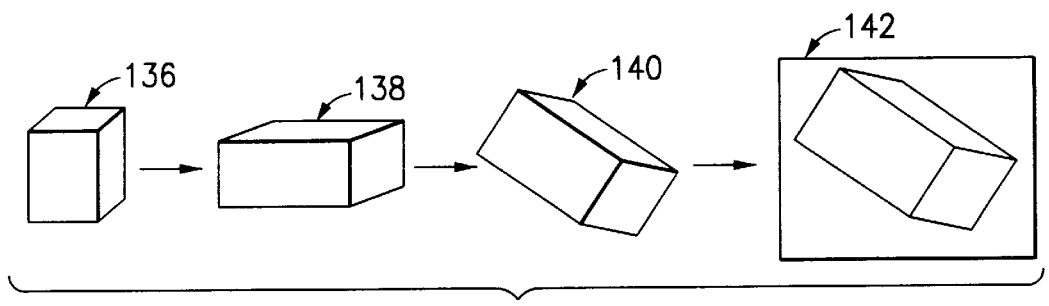
FIG. 11 is a diagram depicting a projection transform procedure employed in a preferred embodiment of the invention.

Although the orientation box can be used in conjunction with any known technique for projecting three-dimensional images from a data volume at arbitrary angles, in accordance with a preferred technique, voxel data is multiplied by aspect scaling factors, rotated by the desired angle and projected onto an image plane. In accordance with a further aspect of the preferred projection technique, scaling factors are used to ensure that voxels which are one unit apart along the X, Y and Z axes in data space are mapped onto pixels that are at most one unit apart along the X and Y axes on the image plane. This process is illustrated in FIG. 11, which shows voxel data 118 being multiplied by aspect scaling (step 120), rotated by the desired angle (step 122) and projected onto the image plane (step 124).

Figure 12:
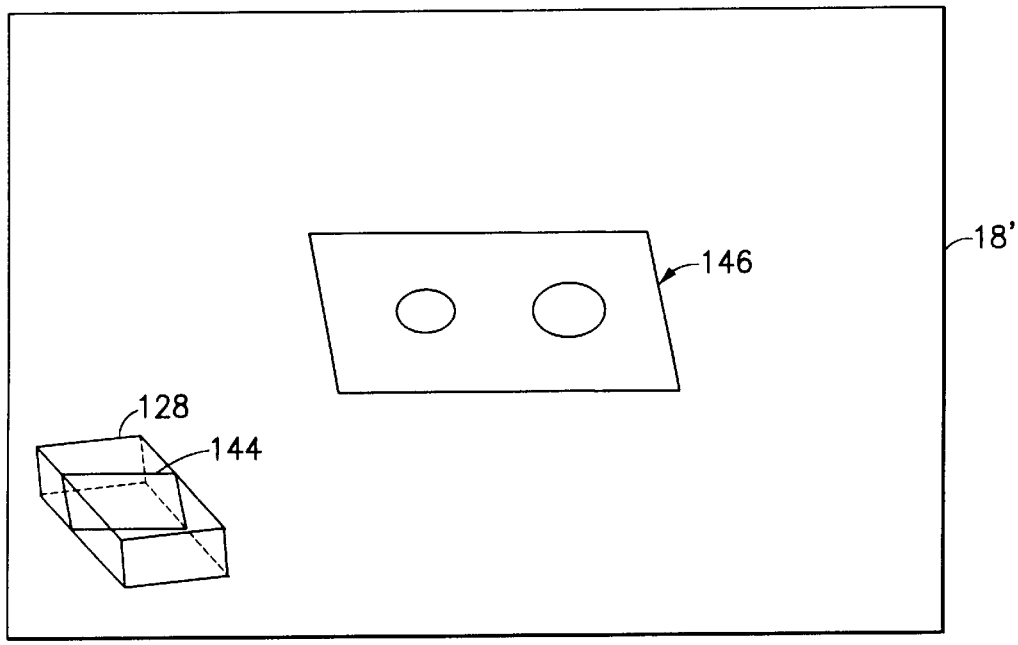
FIG. 12 is a diagram depicting a display of a two-dimensional slice with graphics representing the position and orientation of the slice relative to the data volume.

If the ultrasound imaging system operator desires to see two-dimensional slices through the data volume at the current X, Y, Z rotation orientation, the operator presses the "display mode" key (step 96 in FIG. 8) to change from the "volume rotate" mode to the "cut-plane" (reformat) mode. Referring to FIG. 12, the orientation box 128 changes color (e.g., from green to white) and a colored (e.g., green) polygon 144 appears within the orientation box (step 98 in FIG. 8B) at the center of the data volume. The green color signifies that this portion within the box can be moved. The system then produces an initial representation 146 of a two-dimensional slice through the center of the data set at the current orientation (step 100 in FIG. 8B).

The shape of the slice 146 matches the shape of the green polygon 144 in the orientation box 128. The operator may then use the track-ball to scroll through the data set, displaying successive two-dimensional slices of the data set at the selected orientation and position. As the track-ball is moved (step 102), the green polygon in the orientation box moves (step 104) to visually indicate the location of the slice within the data volume and a display panel is updated to show the location of the slice as a percentage of the total volume (i.e., 50% would be the center of the data volume). When the track-ball stops moving, the system checks the status of the "display mode" key (step 106). If the "display mode" key is not depressed, the display is reformatted by the host computer to show the slice through the data volume at the last slice position when the track-ball stopped moving. If the "display mode" key is depressed, the system exits the "cut plane" mode and enters the "cut plane rotate" mode.

In the "cut plane rotate" mode, the green polygon that indicates the location of the slice through the data volume turns white and the orientation box turns green (step 108), indicating that the slice is now fixed and the data volume may rotate relative to the slice. The system then displays the reformatted slice in the manner previously described (step 110). The user may now rotate the orientation box to a new X, Y, Z orientation by moving the track-ball (step 112). As the user does so, the white polygon changes shape to show the shape of the slice. When the orientation is set, the user depresses the "calculate" key (step 114), which causes the system to display a new two-dimensional slice taken at the angle indicated by the angle of the polygon relative to the orientation box. If the "display mode" key is not depressed (step 116), the operator can reorient the data volume. If the "display mode" key is depressed, the system returns to the "volume rotate" mode.

Algorithms for producing three-dimensional projections of two-dimensional data are well known, as are techniques for reformatting data to produce arbitrary slices through a data set. The projected or reformatted data is output by the host computer to the XY display memory 48 (see FIG. 3). The image frame of projected or reformatted data is then sent to the video processor 16 and captured by the cine memory 54. The video processor superimposes the orientation box and other graphical symbols onto the image frame of projected reformatted data for output to the display monitor.

The foregoing preferred embodiments have been disclosed for the purpose of illustration. Variations and modifications of the concept of the invention will be readily apparent to persons skilled in the art. All such variations and modifications are intended to be encompassed by the claims set forth hereinafter.

We claim:

1. A system for three-dimensional imaging of an object volume having a specular ultrasound reflector inserted therein, comprising:

an ultrasound linear transducer array for transmitting ultrasound beams and detecting ultrasound echoes reflected from said object volume at a multiplicity of sample volumes in a scan plane;

means for controlling said ultrasound linear transducer array to transmit ultrasound beams in a steered direction, said steered direction being such that reflections from said specular ultrasound reflector impinge on said ultrasound linear transducer array;

acquisition means coupled to said ultrasound linear transducer array for acquiring acoustic data derived at least in part from ultrasound echoes transmitted in said steered direction and reflected from each one of a multiplicity of scan planes through said object volume;

means for storing acoustic data for each of a multiplicity of image frames corresponding to said multiplicity of scan planes;

operator interface means for receiving operator inputs;

means for defining a data volume from said acoustic data based on operator inputs;

first mode means responsive to operator inputs for enabling selection in a first mode of an orientation of said data volume relative to an imaging plane;

means for generating first imaging data representing a three-dimensional projection onto said imaging plane by applying a projection transformation to said data volume;

a display monitor comprising an array of pixels; and means for mapping said first imaging data into a first image frame of pixel intensity values for display on said display monitor in said first mode.

2. The system as defined in claim 1, wherein said acquisition means comprise a B-mode processor and said data volume comprises intensity values derived from reflections from respective sample volumes in said object volume.

3. The system as defined in claim 2, wherein said acquisition means further comprise a velocity estimator and said data volume further comprises velocity values derived from reflections from respective sample volumes in said object volume.

4. The system as defined in claim 2, wherein said acquisition means further comprise a power estimator and said data volume further comprises power values derived from reflections from respective sample volumes in said object volume.

5. The system as defined in claim 1, wherein said acquisition means comprise a velocity estimator and said data volume comprises velocity values derived from reflections from respective sample volumes in said object volume.

6. The system as defined in claim 1, wherein said acquisition means comprise a power estimator and said data volume comprises power values derived from reflections from respective sample volumes in said object volume.

7. The system as defined in claim 1, further comprising:
second mode means responsive to operator inputs for enabling selection in a second mode of a first two-dimensional slice of data in said data volume corresponding to a plane in said object volume which intersects said specular ultrasound reflector; and
means for generating second imaging data corresponding to said first two-dimensional slice by reformatting said data volume,
wherein said mapping means map said second imaging data into a second image frame of pixel intensity values for display on said display monitor in said second mode.

8. The system as defined in claim 7, further comprising:
third mode means responsive to operator inputs for enabling selection in a third mode of a second two-dimensional slice of data in said data volume corresponding to a plane in said object volume which is coplanar with said specular ultrasound reflector; and
means for generating third imaging data corresponding to said second two-dimensional slice by reformatting said data volume,
wherein said mapping means map said third imaging data into a third image frame of pixel intensity values for display on said display monitor in said third mode.

9. A system for three-dimensional imaging of an object volume having a specular ultrasound reflector inserted therein, comprising:
an ultrasound linear transducer array comprising a multiplicity of transducer elements;
means for controlling said ultrasound linear transducer array to transmit ultrasound beams in first and second steered directions, said second steered direction being such that reflections from said specular ultrasound reflector impinge on said ultrasound linear transducer array;
acquisition means coupled to said ultrasound transducer array for acquiring first acoustic data derived at least in part from ultrasound echoes transmitted in said first steered direction and reflected from each one of a multiplicity of scan planes through said object volume and for acquiring second acoustic data derived at least in part from ultrasound echoes transmitted in said second steered direction and reflected from each one of said multiplicity of scan planes;
means for storing said first and second acoustic data for each of a multiplicity of image frames corresponding to said multiplicity of scan planes;

operator interface means for receiving operator inputs;
means for defining a data volume of said first and second acoustic data based on operator inputs;
first mode means responsive to operator inputs for enabling selection in a first mode of an orientation of said data volume relative to an imaging plane;
means for generating first imaging data representing a first projection onto said imaging plane by applying a first projection transformation to said first acoustic data in said data volume;
means for generating second imaging data representing a second projection onto said imaging plane by applying a second projection transformation to said second acoustic data in said data volume;
a display monitor comprising an array of pixels;
first mapping means for mapping said first imaging data into a first image frame of pixel intensity values;
second mapping means for mapping said second imaging data into a second image frame of pixel intensity values; and
a video processor for concurrently displaying said first and second image frames on said display monitor in said first mode.

10. The system as defined in claim 9, wherein said acquisition means comprise a B-mode processor for deriving intensity values and a velocity estimator for deriving velocity values, wherein said first acoustic data comprise said intensity values and said second acoustic data comprise said velocity values.

11. The system as defined in claim 9, wherein said acquisition means comprise a B-mode processor for deriving intensity values and a power estimator for deriving power values, wherein said first acoustic data comprise said intensity values and said second acoustic data comprise said power values.

12. The system as defined in claim 9, wherein said first mapping means comprise a gray-scale map and said second mapping means comprise a color map.

13. The system as defined in claim 9, further comprising:
second mode means responsive to operator inputs for enabling selection in a second mode of a first two-dimensional slice of data in said data volume corresponding to a plane in said object volume which intersects said specular ultrasound reflector;
means for generating third imaging data corresponding to said first two-dimensional slice by reformatting said first acoustic data in said data volume; and
means for generating fourth imaging data corresponding to said first two-dimensional slice by reformatting said second acoustic data in said data volume;
wherein said first mapping means map said third imaging data into a third image frame of pixel intensity values, said second mapping means map said fourth imaging data into a fourth image frame of pixel intensity values, and said video processor concurrently displays said third and fourth image frames on said display monitor in said second mode.

14. The system as defined in claim 13, further comprising:
third mode means responsive to operator inputs for enabling selection in a third mode of a second two-dimensional slice of data in said data volume corresponding to a plane in said object volume which is coplanar with said specular ultrasound reflector;
means for generating fifth imaging data corresponding to said second two-dimensional slice by reformatting said first acoustic data in said data volume; and means for generating sixth imaging data corresponding to said second two-dimensional slice by reformatting said second acoustic data in said data volume;

wherein said first mapping means map said fifth imaging data into a fifth image frame of pixel intensity values, said second mapping means map said sixth imaging data into a sixth image frame of pixel intensity values, and said video processor concurrently displays said fifth and sixth image frames on said display monitor in said second mode.

15. A method for three-dimensional imaging of an object volume in which a specular ultrasound reflector is inserted, comprising the steps of:

scanning an ultrasound linear transducer array across said object volume;

operating said ultrasound linear transducer array during said scanning to transmit ultrasound beams in a steered direction, said steered direction being such that reflections from said specular ultrasound reflector impinge on said ultrasound linear transducer array;

acquiring acoustic data derived at least in part from ultrasound echoes transmitted in said steered direction and reflected from each one of a multiplicity of scan planes through said object volume;

storing acoustic data for each of a multiplicity of image frames corresponding to said multiplicity of scan planes;

defining a data volume from said acoustic data;

orienting said data volume relative to an imaging plane;

generating first imaging data representing a three-dimensional projection onto said imaging plane by applying a projection transformation to said data volume; and displaying a first image frame which is a function of said first imaging data.

16. The method as defined in claim 15, wherein said acoustic data comprises B-mode amplitude values.

17. The method as defined in claim 15, wherein said acoustic data comprises color velocity values.

18. The method as defined in claim 15, wherein said acoustic data comprises power Doppler values.

19. The method as defined in claim 15, further comprising the steps of:

selecting a two-dimensional slice of data in said data volume corresponding to a plane in said object volume which is coplanar with said specular ultrasound reflector;

generating second imaging data corresponding to said two-dimensional slice by reformatting said data volume; and displaying a second image frame which is a function of said second imaging data.

20. A method for three-dimensional imaging of an object volume in which a specular ultrasound reflector is inserted, comprising the steps of:

scanning an ultrasound linear transducer array across said object volume;

operating said ultrasound linear transducer array during said scanning to transmit ultrasound beams in first and second steered directions, said second steered direction being such that reflections from said specular ultrasound reflector impinge on said ultrasound linear transducer array;

acquiring first acoustic data derived at least in part from ultrasound echoes transmitted in said first steered direction and reflected from each one of a multiplicity of scan planes through said object volume;

acquiring second acoustic data derived at least in part from ultrasound echoes transmitted in said second steered direction and reflected from each one of said multiplicity of scan planes;

storing said first and second acoustic data for each of a multiplicity of image frames corresponding to said multiplicity of scan planes;

defining a data volume of said first and second acoustic data;

orienting said data volume relative to an imaging plane;

generating first imaging data representing a first projection onto said imaging plane by applying a first projection transformation to said first acoustic data in said data volume;

generating second imaging data representing a second projection onto said imaging plane by applying a second projection transformation to said second acoustic data in said data volume; and concurrently displaying first and second image frames which are functions of said first and second imaging data respectively.

21. The method as defined in claim 20, wherein said first acoustic data comprises B-mode amplitude values and said second acoustic data comprises color velocity values.

22. The method as defined in claim 20, wherein said first acoustic data comprises B-mode amplitude values and said second acoustic data comprises power Doppler values.

23. The method as defined in claim 20, further comprising the steps of:

selecting a two-dimensional slice of data in said data volume corresponding to a plane in said object volume which is coplanar with said specular ultrasound reflector;

generating third imaging data corresponding to said two-dimensional slice by reformatting said first acoustic data in said data volume;

generating fourth imaging data corresponding to said two-dimensional slice by reformatting said second acoustic data in said data volume; and concurrently displaying third and fourth image frames which are functions of said third and fourth imaging data respectively.

24. The method as defined in claim 23, wherein said first acoustic data comprises B-mode amplitude values and said second acoustic data comprises color velocity values.

25. The method as defined in claim 23, wherein said first acoustic data comprises B-mode amplitude values and said second acoustic data comprises power Doppler values.

26. A method for three-dimensional imaging of an object volume in which a specular ultrasound reflector is inserted, comprising the steps of:

scanning an ultrasound linear transducer array across said object volume;

operating said ultrasound linear transducer array during said scanning to transmit ultrasound beams in a steered direction, said steered direction being such that reflections from said specular ultrasound reflector impinge on said ultrasound linear transducer array;

acquiring acoustic data derived at least in part from ultrasound echoes transmitted in said steered direction and reflected from each one of a multiplicity of scan planes through said object volume;

storing acoustic data for each of a multiplicity of image frames corresponding to said multiplicity of scan planes;

defining a data volume from said acoustic data;

selecting a two-dimensional slice of data in said data volume corresponding to a plane in said object volume which is coplanar with said specular ultrasound reflector;

generating imaging data corresponding to said two-dimensional slice by reformatting said data volume; and displaying an image frame which is a function of said imaging data.

27. The method as defined in claim 26, wherein said acoustic data comprises B-mode amplitude values.

28. The method as defined in claim 26, wherein said acoustic data comprises color velocity values.

29. The method as defined in claim 27, wherein said acoustic data comprises power Doppler values.

30. A method for three-dimensional imaging of an object volume in which a specular ultrasound reflector is inserted, comprising the steps of:

scanning an ultrasound linear transducer array across said object volume;

operating said ultrasound linear transducer array during said scanning to transmit ultrasound beams in first and second steered directions, said second steered direction being such that reflections from said specular ultrasound reflector impinge on said ultrasound linear transducer array;

acquiring first acoustic data derived at least in part from ultrasound echoes transmitted in said first steered direction and reflected from each one of a multiplicity of scan planes through said object volume;

acquiring second acoustic data derived at least in part from ultrasound echoes transmitted in said second steered direction and reflected from each one of said multiplicity of scan planes;

storing said first and second acoustic data for each of a multiplicity of image frames corresponding to said multiplicity of scan planes;

defining a data volume of said first and second acoustic data;

selecting a two-dimensional slice of data in said data volume corresponding to a plane in said object volume which is coplanar with said specular ultrasound reflector;

generating first imaging data corresponding to said two-dimensional slice by reformatting said first acoustic data in said data volume;

generating second imaging data corresponding to said two-dimensional slice by reformatting said second acoustic data in said data volume; and concurrently displaying first and second image frames which are functions of said first and second imaging data respectively.

31. The method as defined in claim 30, wherein said first acoustic data comprises B-mode amplitude values and said second acoustic data comprises color velocity values.

32. The method as defined in claim 30, wherein said first acoustic data comprises B-mode amplitude values and said second acoustic data comprises power Doppler values.

33. A system for three-dimensional imaging of an object volume in which a specular ultrasound reflector is inserted, comprising an ultrasound linear transducer array, a display monitor and a data processor programmed to perform the following steps:

operating said ultrasound linear transducer array during to transmit ultrasound beams in a steered direction, said steered direction being such that reflections from said specular ultrasound reflector impinge on said ultrasound linear transducer array;

acquiring acoustic data derived at least in part from ultrasound echoes transmitted in said steered direction and reflected from each one of a multiplicity of scan planes through said object volume;

storing acoustic data for each of a multiplicity of image frames corresponding to said multiplicity of scan planes;

defining a data volume from said acoustic data;

orienting said data volume relative to an imaging plane;

generating first imaging data representing a three-dimensional projection onto said imaging plane by applying a projection transformation to said data volume; and displaying a first image frame which is a function of said first imaging data on said display monitor.

34. A system for three-dimensional imaging of an object volume in which a specular ultrasound reflector is inserted, comprising an ultrasound linear transducer array, a display monitor and a data processor programmed to perform the following steps:

operating said ultrasound linear transducer array during to transmit ultrasound beams in first and second steered directions, said second steered direction being such that reflections from said specular ultrasound reflector impinge on said ultrasound linear transducer array;

acquiring first acoustic data derived at least in part from ultrasound echoes transmitted in said first steered direction and reflected from each one of a multiplicity of scan planes through said object volume;

acquiring second acoustic data derived at least in part from ultrasound echoes transmitted in said second steered direction and reflected from each one of said multiplicity of scan planes;

storing said first and second acoustic data for each of a multiplicity of image frames corresponding to said multiplicity of scan planes;

defining a data volume of said first and second acoustic data;

orienting said data volume relative to an imaging plane;

generating first imaging data representing a first projection onto said imaging plane by applying a first projection transformation to said first acoustic data in said data volume;

generating second imaging data representing a second projection onto said imaging plane by applying a second projection transformation to said second acoustic data in said data volume; and concurrently displaying first and second image frames which are functions of said first and second imaging data respectively on said display monitor.

35. A system for three-dimensional imaging of an object volume in which a specular ultrasound reflector is inserted, comprising an ultrasound linear transducer array, a display monitor and a data processor programmed to perform the following steps:

operating said ultrasound linear transducer array during to transmit ultrasound beams in a steered direction, said steered direction being such that reflections from said specular ultrasound reflector impinge on said ultrasound linear transducer array;

acquiring acoustic data derived at least in part from ultrasound echoes transmitted in said steered direction and reflected from each one of a multiplicity of scan planes through said object volume;

storing acoustic data for each of a multiplicity of image frames corresponding to said multiplicity of scan planes;

defining a data volume from said acoustic data;

selecting a two-dimensional slice of data in said data volume corresponding to a plane in said object volume which is coplanar with said specular ultrasound reflector;

generating imaging data corresponding to said two-dimensional slice by reformatting said data volume; and displaying an image frame which is a function of said imaging data on said display monitor.

36. A system for three-dimensional imaging of an object volume in which a specular ultrasound reflector is inserted, comprising an ultrasound linear transducer array, a display monitor and a data processor programmed to perform the following steps:

operating said ultrasound linear transducer array during to transmit ultrasound beams in first and second steered directions, said second steered direction being such that reflections from said specular ultrasound reflector impinge on said ultrasound linear transducer array;

acquiring first acoustic data derived at least in part from ultrasound echoes transmitted in said first steered direction and reflected from each one of a multiplicity of scan planes through said object volume;

acquiring second acoustic data derived at least in part from ultrasound echoes transmitted in said second steered direction and reflected from each one of said multiplicity of scan planes;

storing said first and second acoustic data for each of a multiplicity of image frames corresponding to said multiplicity of scan planes;

defining a data volume of said first and second acoustic data;

selecting a two-dimensional slice of data in said data volume corresponding to a plane in said object volume which is coplanar with said specular ultrasound reflector;

generating first imaging data corresponding to said two-dimensional slice by reformatting said first acoustic data in said data volume;

generating second imaging data corresponding to said two-dimensional slice by reformatting said second acoustic data in said data volume; and concurrently displaying first and second image frames which are functions of said first and second imaging data respectively on said display monitor.

* * * * *